(12) United States Patent
Hell et al.

(10) Patent No.: US 6,412,979 B1
(45) Date of Patent: Jul. 2, 2002

(54) COMPUTED TOMOGRAPHY SYSTEM WITH ARRANGEMENT FOR COOLING THE X-RAY RADIATOR MOUNTED ON A ROTATING GANTRY

(75) Inventors: Erich Hell; Detlef Mattern, both of Erlangen; Thomas Ohrndorf, Altendorf; Peter Schardt, Roettenbach, all of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/412,127

(22) Filed: Oct. 5, 1999

(30) Foreign Application Priority Data

Oct. 5, 1998 (DE) .......................... 198 45 756

(51) Int. Cl.⁷ .............................................. H01J 35/10
(52) U.S. Cl. ......................... 378/200; 378/130; 378/199
(58) Field of Search ................................ 378/130, 199, 378/200

(56) References Cited

U.S. PATENT DOCUMENTS

| | | | |
|---|---|---|---|
| 4,115,697 A | | 9/1978 | Hounsfield et al. ........... 378/15 |
| 5,313,512 A | * | 5/1994 | Tanaka ........................ 378/200 |
| 5,610,968 A | | 3/1997 | Deucher et al. ............. 378/199 |
| 5,703,926 A | * | 12/1997 | Bischof ....................... 378/200 |
| 5,732,123 A | * | 3/1998 | Peralta et al. ................ 378/199 |
| 5,883,936 A | | 3/1999 | Hell et al. ................... 378/125 |
| 5,956,383 A | * | 9/1999 | Kendall ....................... 378/199 |
| 6,084,942 A | * | 7/2000 | Hell et al. ................... 378/200 |
| 6,254,272 B1 | * | 7/2001 | Dilick ........................ 378/200 |

FOREIGN PATENT DOCUMENTS

DE  OS 197 48 281  5/1998

* cited by examiner

Primary Examiner—Robert H. Kim
Assistant Examiner—Allen C. Ho
(74) Attorney, Agent, or Firm—Schiff Hardin & Waite

(57) ABSTRACT

A computed tomography system has a gantry rotating around a patient acceptance space in a stationary gantry housing, the gantry carrying an x-ray radiator connected to a cooling device. The x-ray tube is a directly cooled rotating bulb tube whose coolant serves as an intermediate heat store and which is cooled in standstill periods of the gantry by a likewise co-rotating heat exchanger via a coolant pump.

8 Claims, 3 Drawing Sheets

COMPUTED TOMOGRAPHY SYSTEM WITH ARRANGEMENT FOR COOLING THE X-RAY RADIATOR MOUNTED ON A ROTATING GANTRY

BACKGROUND OF THE INVENTION

1. Field of the Invention

The present invention is directed to a computed tomography system of the type having a gantry rotating around a patient acceptance space in a stationary gantry housing, the gantry carrying an x-ray source connected to a cooling device.

2. Description of the Prior Art

99% of the energy utilized in generating x-rays is converted into heat, the elimination thereof presenting rather substantial problems particularly in modem examination installations such as computed tomography or angiography systems wherein extremely high powers are used. A particular problem arises in computed tomography from the fact that the x-ray source is located on a continuously rotating gantry, and the rotational axis is not accessible for rotary bushings because of the necessary clearance for pushing the patient through. Although the electrical energy can be easily supplied via wiper rings, the waste heat, however, cannot be eliminated by direct cooling with fluid during the rotary motion.

Heretofore, rotating anode x-ray tubes have been generally employed in computed tomography systems, which intermediately store the arising heat in the anode dish and permanently emit it mainly via thermal radiation (convection) to the surrounding cooling and insulating oil. After reaching the anode limit temperature, long compulsory pauses must always take place in order to be able to adequately cool the anode dish by radiation via the relatively poor means of thermal radiation. The oil circulates in a closed circulation loop through a co-rotating heat exchanger that outputs the heat to the air in the gantry housing. Another stationary heat exchanger in the gantry housing cools the heated gantry air and eliminates the heat to, for example, a permanently installed liquid coolant system. Given this known structure, two high thermal resistances necessarily lie in series: the primarily radiant transport from the rotating anode through the tube vacuum into the cooling oil, and the two heat exchangers that decouple the gantry rotation.

Due to the $T^4$ law the radiation transport is in fact rather efficient at high dish temperatures (around 2000° C.), but decreases greatly given dropping temperature and the existing heat capacity of the dish is not completely utilized for time reasons. The two series oil/air and air/water heat exchangers must be rather bulky because of the low heat capacity of the air and because of only a slight, allowable temperature increase of the air.

U.S. Pat. No. 4,115,697 discloses a computed tomography system wherein a circulation loop for a liquid coolant surrounding the x-ray source and having a circulating pump, a radiator and a reservoir is provided on the gantry. In standstill periods of the gantry, the radiator is arranged in the airstream of a blower.

U.S. Pat. No. 5,610,968 discloses a computed tomography system having an x-ray source connected via a first heat exchanger, operated at the primary and secondary sides with liquid, to the primary side of a second heat exchanger, operated with liquid at the primary side and with air at the secondary side. The second heat exchanger is active during standstill periods of the gantry in order to cool the liquid flowing in a circulation loop including the secondary side of the first heat exchanger and the primary side of the second heat exchanger, cooling taking place via the secondary side of the second heat exchanger.

German OS 197 48 281 is directed to a cooling device for employment with an x-ray source in a computed tomography system, that has a heat exchanger attached on the gantry that is traversed at the primary side by a liquid coolant in thermal contact with the x-ray source and operating with air at the secondary side.

SUMMARY OF THE INVENTION

An object of the present invention is to provide a computed tomography system of the type initially described having improved cooling achieved with only short standstill times after an examination, in order to return the system to the desired initial temperatures.

A further object of the invention is to provide a computed tomography system of the type initially described wherein effective cooling of the x-ray radiator and the x-ray tube contained therein, is assured with a small installation space.

These objects are inventively achieved in a computed tomography system having a gantry rotatable around a patient acceptance space in a stationary gantry housing, the gantry carrying an x-ray radiator containing an x-ray tube in thermal contact with a liquid coolant, the x-ray radiator being connected to a heat exchanger that is attached to the gantry and which has a primary side and a secondary side. Liquid coolant flows In a primary circulation loop that includes the primary side of the heat exchanger and a coolant pump pumps the liquid coolant through the primary circulation loop in standstill periods of the gantry for cooling. A liquid coolant flows through the secondary side of the heat exchanger, this liquid coolant being supplied to the secondary side in standstill periods of the gantry from a source that is stationary with respect to the gantry and being supplied from the secondary side to a sink that is stationary with respect to the gantry.

An important feature of the invention is that the heat exchanger attached to the gantry, and therefore rotating with the gantry during the implementation of an examination is not constantly active, which would make it necessary to employ air as the coolant at the secondary side. Instead, the heat exchanger is only placed into operation during standstill periods of the gantry, so that a liquid coolant, preferably water, can be employed at the secondary side of the heat exchanger, since this is supplied to the secondary side of the heat exchanger from a source that is stationary relative to the gantry and flows from the secondary side of the heat exchanger to a sink that is stationary relative to the gantry. The source and the sink for the liquid coolant thus can be components of a circulation loop for the coolant which also has a cooling device for the liquid coolant that is stationary relative to the gantry. As a result of employing a liquid coolant at the secondary side of the heat exchanger, the heat exchanger exhibits only slight dimensions compared to a heat exchanger that operates with liquid at the primary side and with air at the secondary side. Moreover, the thermal resistance to be overcome in a heat exchanger operating with liquid both at the primary side and at the secondary side is lower, so that a more effective cooling of the x-ray radiator, or of the x-ray tube, is assured be the inventive computed tomography system.

In a preferred embodiment of the Invention, an x-ray radiator Is used that contains a rotating bulb tube as the x-ray tube. In x-ray radiators constructed according to this principle, the anode of the x-ray tube is in direct contact with the liquid coolant that is present at the primary side of the heat exchanger, efficient cooling of the anode thereby being assured. Following the end of the examination of a patient, the anode of a rotating bulb tube, due to the direct contact with the liquid coolant, is already at essentially the same temperature as the liquid coolant after a relatively short time, for example approximately thirty seconds. Therefore, the anode of the rotating bulb tube differing from a rotating anode tube whose anode is cooled by convection does not have to function as a heat store. This function is assumed instead by the liquid coolant located in the primary circulation loop, this generally being oil, particularly insulating oil.

The anode of the rotating bulb tube at most serves as brief-duration heat store.

In order to assure an adequate heat capacity, it can be provided in a version of the invention the primary circulation loop contains an additional coolant storage tank mounted on the gantry.

A fast coupling, implemented preferably as a fast magnetic coupling having at least one electromagnet, is provided, which in a defined rotary position of the gantry, connects lines connected to the secondary side of the heat exchanger and arranged on the gantry for the coolant, to lines coming from the source and leading to the sink that are attached to the gantry housing. Whenever, after the implementation of an examination, the x-ray tube of the x-ray radiator and the rotation of the gantry are deactivated, the gantry is automatically moved into the defined position wherein, as a result of the fast coupling, a connection of the source that is stationary relative to the gantry and the sink of the liquid coolant that is stationary relative to the gantry ensues to the heat exchanger which rotates together with the gantry, so that the thermal energy stored therein that has arisen during the examination can be taken from the liquid coolant within a short time span. As a result, practically no standstill times of the computed tomography system occur, since the time required for removing a patient and for positioning the next patient on the displaceable bed is usually already adequate in order to achieve a cooling of the coolant serving as intermediate heat store.

According to one version of the invention, a coolant displacer that is preferably operated by compressed air is provided for emptying the secondary side of the heat exchanger and the lines for the liquid coolant that are connected thereto and arranged on the gantry. After the coolant has cooled, the flow of the liquid coolant is initially interrupted at the secondary side of the heat exchanger and any coolant which may be present in the secondary side of the heat exchanger and in lines connected thereto is removed, so that substantially no coolant is present at the secondary side of the heat exchanger during a subsequent examination. Such coolant, if present, could cause malfunctions of the computed tomography system, for example due to leakage from the secondary side.

DESCRIPTION OF THE PREFERRED EMBODIMENTS

Figure 1:
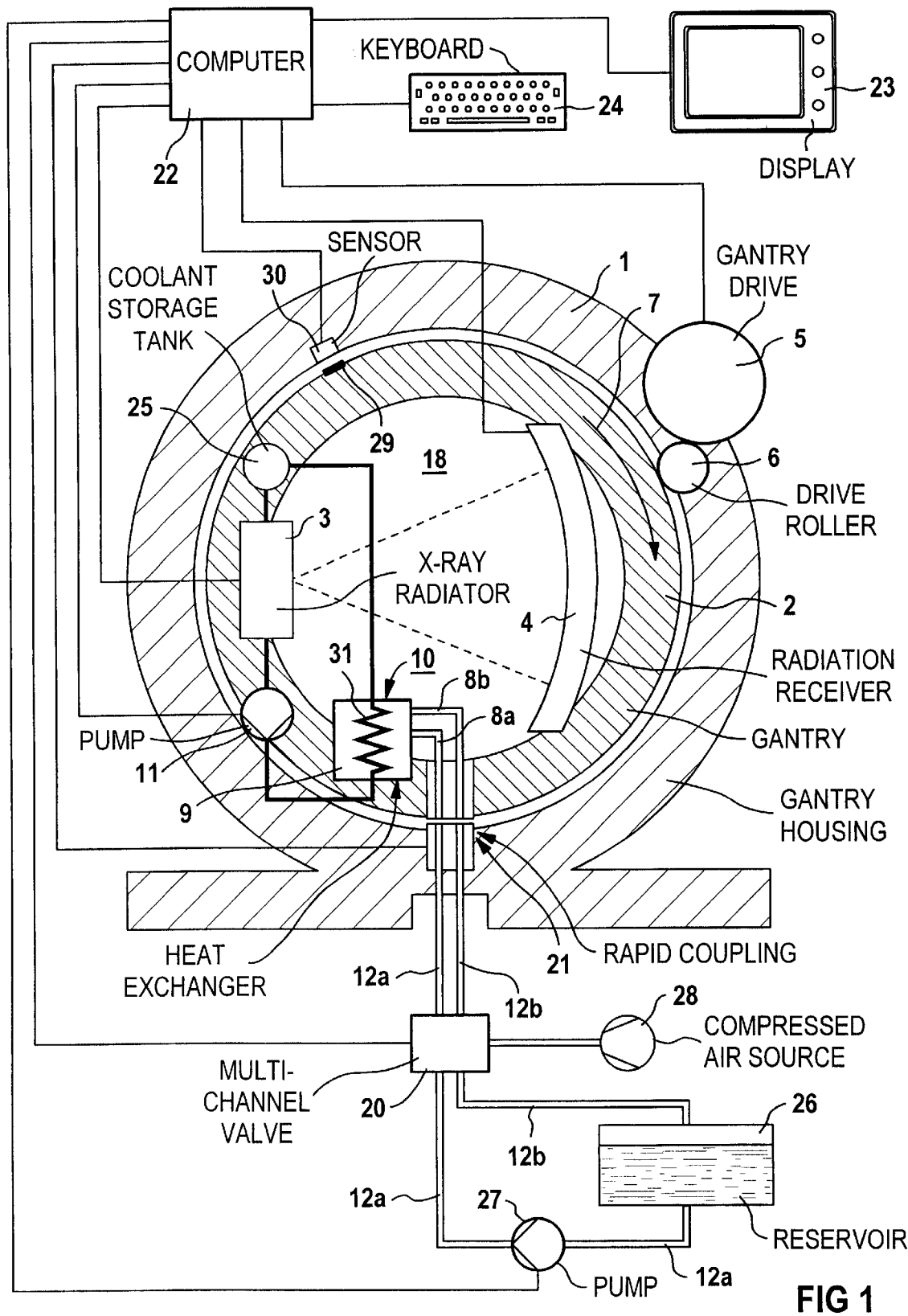
FIG. 1 is a schematic illustration of an inventive computed tomography system.

FIG. 1 schematically shows an inventive computed tomography system that, arranged in a known way, has a gantry 2 rotatably mounted in a stationary gantry housing 1, with an x-ray radiator 3 and, opposite thereto, a radiation receiver 4 being mounted on gantry 2. The gantry 2 can be placed into rotation in the direction of the arrow 7 by a motorized gantry drive 5 via a drive roller 6.

When, given a rotating gantry 2 and an active x-ray radiator 3, a patient is located in the patient acceptance space 18 surrounded by the gantry 2, a number of projections is registered with the radiation receiver 4. The output data of the radiation receiver 4 corresponding to these projections are supplied to a computer 22 that calculates a tomogram of the patient therefrom and displays this on a display 23.

The computer 22 serves for the control of the entire computed tomography system, and therefore has a keyboard 24 connected to it, via which commands required for the operation of the computed tomography system can be entered.

The x-ray radiator 3, the radiation receiver 4 and the gantry drive 5 are also connected to the computer 22.

Figure 3:
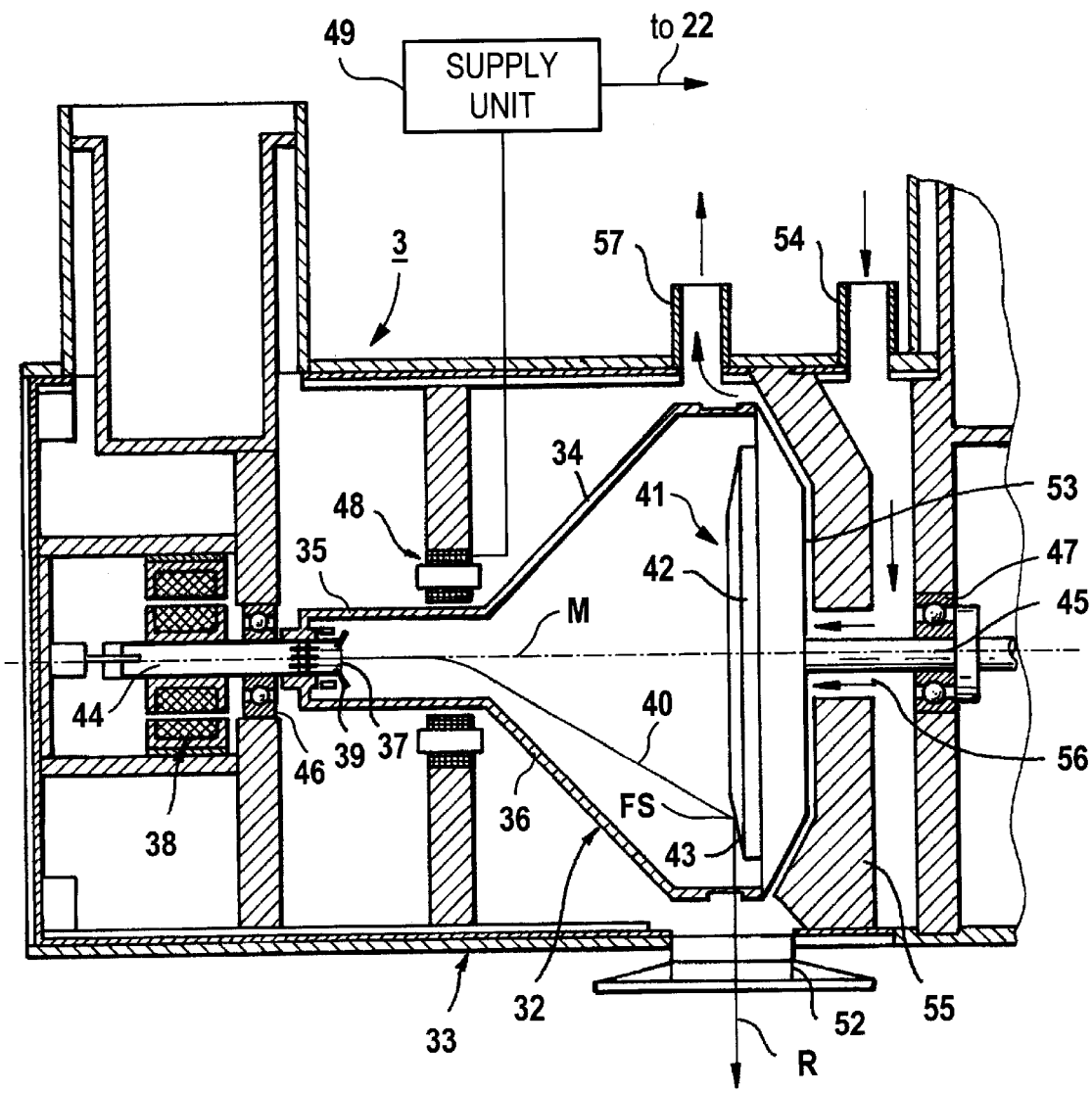
FIG. 3 is a schematic illustration of an x-ray radiator having a rotating bulb tube, as employed in the computed tomography system according to FIGS. 1 and 2.

The x-ray radiator 3 is of the type shown as an example in FIG. 3, containing a rotating bulb tube 32. The anode 41 of the rotating bulb tube 32 is thus in direct contact with liquid coolant, for example insulating oil, that is contained in a protective housing 33 surrounding the rotating bulb tube 32 and serves as a heat store during the implementation of an examination.

The liquid coolant flows in a primary circulation loop that includes the primary side of a heat exchanger introduced on the gantry 2, schematically indicated in FIG. 1 as a tube coil and a coolant pump 11. The circulation loop also includes the lines schematically indicated in FIG. 1, one of which connects the protective housing at the x-radiator 3 to the coolant pump 11, and a further one of which connects the coolant pump 11 to one connection of the primary side 31 of a heat exchanger 10, and another one of which connects the other connection of the primary side 31 of the heat exchanger 10 to the protective housing of the x-ray radiator 3. A coolant storage tank 25 that increases the volume of the liquid coolant which is present in the primary circulation loop, and thus increases the heat-storing capacity of the primary circulation loop can be inserted into one of the total of the lines rotating with the gantry 2, preferably the last-mentioned line, in the way shown in FIG. 1.

Two lines 8a and 8b are connected to the secondary side of the heat exchanger 10, that is shown in FIG. 1 as a hollow member 9 surrounding the primary side 31. The two lines 8a and 8b lead to a rapid magnetic coupling 21 that in turn connects the lines 8a and 8b to two lines 12a and 12b terminating at the stationary gantry housing 1 in an operating condition of the computed tomography system that is yet to be described.

Via a multi-channel valve 20 that is, for example, electromagnetically actuated, the lines 12a and 12b lead to a reservoir 26 that is stationary relative to the gantry 2 and that contains a liquid coolant, for example water, with a conveying pump 27 connected into the line 12a.

The multi-channel valve 20 can assume two positions. In the first position, liquid coolant can be conveyed—when the fast magnetic coupling 21 is closed—with the conveying pump 27 in a circulation loop from the reservoir 26 through the secondary side 9 of the heat exchanger 10 and from this point back to the reservoir 26, which is thus both a source and a sink for the liquid coolant. In the second position, the line 12a is uninterrupted and the section of the line 12a connecting the multi-channel valve 20 to the secondary side of the heat exchanger 10 is connected to a compressed air source 28, so that the liquid coolant located in this section of the line 12a, in the secondary side of the heat exchanger 10 and the line 12b can be forced back into the reservoir 26 by a compressed air surge toward the reservoir 26, before the fast magnetic coupling 21 is decoupled. In order to enable an escape of compressed air from the reservoir 26, the multi-channel valve 20 leaves the end of the section of the line 12a situated between the reservoir 26 and the magnetic valve 20 at the magnetic valve side open in its second position.

A mark 29 is attached to the gantry 2, and a stationary sensor 30 attached to the gantry housing 1 emits a signal to the computer 22 when the mark 29 is located in front of the sensor 30. The mark 29 is arranged such that it is located in front of the sensor 30 when the gantry 2 assumes a defined angular position relative to the gantry housing 1 wherein a closing of the rapid magnetic coupling 21, and thus a connection of the line 8a to the line 12a and of the line 8b to the line 12b, is possible.

Figure 2:
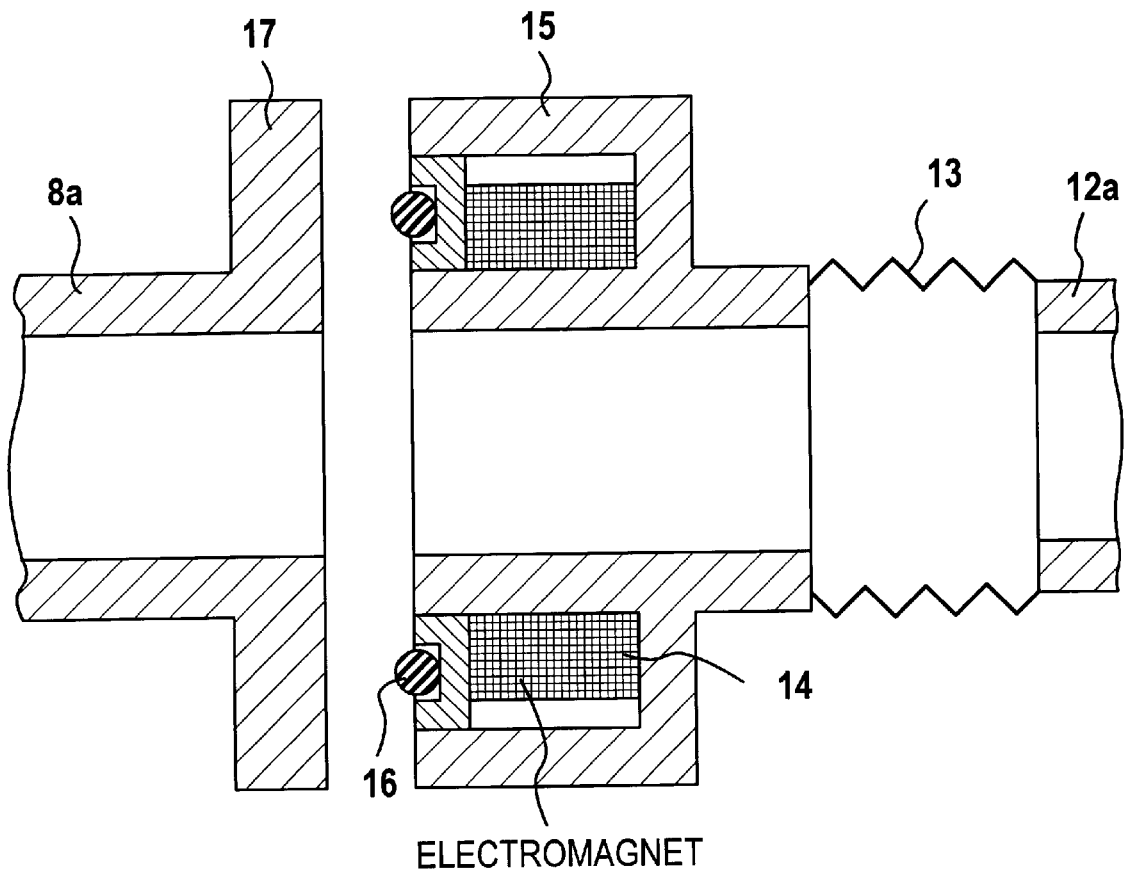
FIG. 2 is an enlarged illustration of the magnetic coupling for connecting the cooling lines of the gantry to the stationary lines of the external cooler in accordance with the invention.

FIG. 2 shows half of the rapid magnetic coupling 21, that serves the purpose of connecting the line 8a to the line 12a. As can be seen from FIG. 2, that region of the line 12a located immediately in front of the rapid magnetic coupling 21 is fashioned as an axially resilient corrugated tube 13 to which a sealing head 15 that accepts an electromagnet 14 is attached. When an excitation current flows through the electromagnet 14, the sealing head 15 is magnetically attracted to the flange 17 and an O-ring 16 is seated against the flange 17 in sealing fashion, the flange 17 being located at the free end of the line 8a. The corrugated tube 13 is thereby elastically stretched axially. A liquid-tight connection now exists between the line 12a and the line 8a. When the excitation current through the electromagnet 14 is shut off, a separation of the sealing head 15 from the flange 17 ensues as a consequence of the fact that the elastic lengthening of the corrugated pipe 13 retracts. The gap between the sealing head 15 from the flange 17 illustrated in FIG. 2 is then present, so that the gantry 2 can rotate unimpeded.

The structure of the other half of the rapid magnetic coupling responsible for the lines 8b and 12b corresponds to the structure according to FIG. 2, with the activation and deactivation of the two halves of the rapid magnetic coupling 21 ensuing synchronously.

The two electromagnets 14 of the rapid magnetic coupling 21, the multi-channel valve 20, the conveying pump 27 and the sensor 30 are likewise connected to the computer 22.

During operation of the computed tomography system, i.e. when a patient is located in the patient acceptance space 18, the gantry 2 rotates around the patient acceptance space 18 for registering the projections required for the reconstruction of a tomogram of the patient. The heat that the x-ray radiator 3 produces while it is active during the examination is absorbed by the liquid coolant located in the primary circulation loop and is intermediately stored. The computer 22, in order to assure a uniform temperature of the liquid coolant and thus in order to make complete use of the heat capacity of the liquid coolant located in the primary circulation loop, activates the coolant pump 11. After the end of the examination, the computer 22 stops the rotation of the gantry 2 and, dependent on the output signal of the sensor 30, brings the gantry 2 into the position relative to the gantry housing 1 illustrated in FIG. 1. The computer 22 now actuates the rapid magnetic coupling 21 such that the lines 8a and 8b are connected to the lines 12a and 12b, and places the multi-channel value 20 into that position wherein the liquid coolant located in the reservoir 26 can circulate through the secondary side 9 of the heat exchanger 10, and correspondingly activates the conveying pump 27. Since the computer 22 continues to keep the coolant pump 11 activated, the liquid coolant flowing through the secondary side of the heat exchanger 10 withdraws the heat stored in the primary circulation loop and thus stored in the liquid coolant flowing through the primary side of the heat exchanger 10.

When the liquid coolant located in the primary circulation has adequately cooled, the computer 22 stops the conveying pump 27 and places the multi-channel valve 20 into the second position, so that the liquid coolant located in the secondary side of the heat exchanger 10 as well as in the lines connected thereto is conveyed back into the reservoir 26 by the compressed air deriving from the compressed air source 28.

The computer 22 then places the multi-channel valve 20 back into its first position wherein the compressed air source 28 is blocked. Moreover, the computer 22 interrupts the excitation current through the electromagnets 14 of the fast magnetic coupling 21, so that the lines 8a and 8b are again separated from the lines 12a and 12b and the gantry 2 can freely rotate for the implementation of the next examination.

It would be possible to forego the compressed air source 28 and, instead, to close the lines 8a and 8b with suitable measures when the rapid magnetic coupling 21 is separated in order to keep the liquid coolant in the secondary side 9 of the heat exchanger 10 contained therein. Such a procedure, however, is at best less advantageous, at least in the case of water as the liquid current, since there is the risk that the secondary side 9 of the heat exchanger 10 would burst under the pressure of the overheated water located therein.

As shown in FIG. 3, the x-ray radiator 3 has a protective housing 33 wherein a rotating bulb tube 32 is rotatably seated around the center axis M of the arrangement. A rotating bulb tube of this type is disclosed in U.S. Pat. No. 5,883,936, the teachings of which are incorporated herein by reference.

The rotating bulb tube 32 has a bulb-like, insulating vacuum housing 34 with a substantially cylindrical region 35 and a section 36 adjoining thereto that expands like a conical frustum.

A cathode 37 as an electron emitter is arranged at the free end of the cylindrical region 35 of the vacuum housing 34, the cathode 37 being connected via a transformer 38 to a filament current source (not shown) and, via a pin-shaped wiper contact, to the negative pole of a high-voltage generator (not shown). The cathode 37 has a focusing electrode 39 allocated to it that serves the purpose of setting the cross-sectional size of the electron beam 40 that is emitted by the cathode 37 during operation. In a way that is not shown, the focusing electrode is connected to a voltage for producing the desired cross-sectional size of the electron beam 40.

An anode 41 that forms the termination of the vacuum housing 34, evacuated in the inside, is provided at that end of the vacuum housing 34 lying opposite the cathode 37. The anode 41 has an anode dish 42 with an anode edge 43 that, for example, is covered with tungsten.

The vacuum housing 34 with the anode 41 is fashioned substantially rotational symmetrically with reference to the center axis M and has respective shaft stubs 44, 45 at its opposite ends. For rotatable seating of the rotating bulb tube 32, i.e. of the vacuum housing 34 with the cathode 37 together with focusing electrode 39 and the anode 41, in the protective housing 33, bearing elements, for example roller bearings 46 and 47, that accept the shaft stubs 44, 45 are provided. Drive means (not shown in FIG. 3) are provided in order to be able to place the rotating bulb tube 32 into rotation during operation of the x-ray radiator 3.

The anode 41 is electrically insulated from the cathode 37 a and is at ground potential in a single-pole operating mode and is at positive potential given two-pole operation. As a consequence of the tube voltage across the cathode 37 and the anode 41, an electrical field is established between the cathode 37 and the anode 41 that serves for accelerating the electrons emitted by the cathode 37 in the form of the electron beam 40 in the direction onto the anode 41.

The electron beam 40 emanating from the cathode 37, which corresponds to the tube current, exhibits substantially circular cross-section in the case of the described exemplary embodiment because of the substantially rotational-symmetrical fashioning of cathode 37 and focusing electrode 39. In order to assure that the electron beam 40 strikes the conical frustum-shaped anode edge 43 in a defined focal spot referenced FS in order to generate x-rays. A magnet system 48 is provided that surrounds the cylindrical region 35 of the vacuum housing 34 and is secured in the protective housing 33 and, accordingly, does not rotate with the vacuum housing 34 during operation. The magnet system 48 is supplied with electrical signals by a supply unit 49, to generate a dipole field with a quadrupole field superimposed thereon.

Together with the focusing electrode 39, the quadrupole field serves the purpose of focusing the electron beam 40, and thus of realizing a focal spot having a defined size. The dipole field serves the purpose of deflecting the electron beam 40 such that the focal spot FS arises at a defined location on the anode edge 43. The electrical signals supplied to the magnet system 48 from the supply unit 49 connected to the computer 22 can be set with the computer 22 in order to be able to set the focusing and the deflection of the electron beam 40.

The x-rays radiation emanating from the focal spot FS and indicated by an arrow R in FIG. 3 emerge from the vacuum housing 34 in a region of reduced wall thickness and emerge from the protective housing 33 through a beam exit window 52.

A liquid coolant indicated by arrows flows around the exterior 53 of the anode 41. This liquid coolant fills the protective housing 33 at least in that region wherein the vacuum housing 34 is located. The coolant serves the purpose of eliminating the thermal energy arising during generation of the x-ray, this being on the order of magnitude of 99% of the electrical energy supplied to the rotating bulb tube 32.

The protective housing 33 has a coolant inlet 54 connected to a connection of the primary side 31 of the heat exchanger 10, the liquid coolant coming from the heat exchanger 10 entering into the protective housing 33 via this coolant inlet 54. The liquid coolant flows from an inflow opening 56 provided in a partition 55 along the vacuum housing 33 to a coolant outlet 57 from which it flows back to the other connection of the primary side 31 of the heat exchanger 10.

In the described exemplary embodiment, the coolant pump 11 is located between the coolant inlet 54 and the heat exchanger 10, and the coolant storage tank 25 is located between the coolant outlet 57 and the heat exchanger 10. Other arrangements, however, are possible.

In the described exemplary embodiment, the coolant pump 11 is allocated to the x-ray radiator 3. This can be eliminated when an x-ray radiator 3 is employed that is constructed such that the liquid coolant is conveyed as a result of the rotation of the rotating bulb tube in the protective housing. When such an x-radiator is employed, the rotating bulb tube must always rotate at times when, as recited in conjunction with the above-described exemplary embodiment, the coolant pump 11 would be activated in order to assure the circulation of the liquid coolant in the primary circulation 31.

In the described exemplary embodiment, the reservoir 26 is both a source and a sink for the liquid coolant flowing in the secondary circulation 9. This need not necessarily be the case. There is also the possibility of forming the source and the sink separately, for example using a normal water connection as the source and a normal water drain as the sink, in which case a closed secondary circulation loop is no longer present.

The computed tomography system according to the above-described exemplary embodiment is a system of the third generation, I.e. the x-ray radiator 3 and the radiation receiver 4 rotate in common together with the gantry 2. The invention, however, can also be employed in conjunction with other generations of computed tomography systems.

Instead of a rotating bulb tube of the type shown in FIG. 3 having a centrally arranged, co-rotating cathode and a magnet system serving the purpose of deflecting the electron beam, a rotating bulb tube of some other type can be employed in the x-ray radiator 3, for example a rotating bulb tube wherein the cathode is eccentrically arranged relative to the rotational axis, is rotatably seated in the vacuum housing, and is held in a stationary position relative to the rotating vacuum housing by, for example, a magnetic holding device.

The invention is of particular significance for those computed tomography systems wherein, in addition to the rotation of the gantry 2 around the patient acceptance space, a displacement of the gantry 2 and of the patient in the direction of the rotational axis of the gantry 2 ensues relative to one another at the same time, in order to be able to implement spiral scans for volume examinations, since the load on the x-ray tube, and thus the dissipated heat that arises, are particularly high in such a case.

A computed tomography system provided for medical application has been described in the exemplary embodiment. The application of the invention, however, is not limited to the medical field; it can also be used in non-medical areas, for example for non-destructive material inspection or baggage inspection.

Although modifications and changes may be suggested by those skilled in the art, it is the intention of the inventors to embody within the patent warranted hereon all changes and modifications as reasonably and properly come within the scope of their contribution to the art.

We claim as our invention:

1. A computed tomography system comprising:
   a stationary gantry housing in which a rotatable gantry is mounted, said gantry rotating around a patient acceptance space;
   an x-ray radiator mounted on said gantry for co-rotation therewith, said x-ray radiator containing an x-ray tube and liquid coolant in thermal contact with said x-ray tube;

a heat exchanger mounted on said gantry and being co-rotatable therewith, said heat exchanger having a primary side and a secondary side;

a primary circulation loop for said liquid coolant, said primary circulation loop being connected to said x-ray radiator and including said primary side of said heat exchanger;

a coolant pump connected in said primary circulation loop for pumping said liquid coolant through said primary circulation loop for cooling said x-ray tube during standstill periods of said gantry;

a source of a further liquid coolant; and a secondary circulation loop connected to said source of further liquid coolant and including said secondary side of said heat exchanger for supplying said further liquid coolant to said secondary side only during said standstill periods and for circulating said further liquid coolant to a sink that is stationary.

2. A computed tomography system as claimed in claim 1 wherein said x-ray tube comprises a rotating bulb x-ray tube.

3. A computed tomography system as claimed in claim 1 further comprising a coolant storage tank connected in said primary circulation loop and mounted on said gantry.

4. A computed tomography system as claimed in claim 1 wherein said secondary side of said heat exchanger has fluid lines proceeding therefrom and terminating at an exterior of said gantry, and wherein said source of further liquid coolant and said sink have fluid lines proceeding therefrom and terminating at an interior of said gantry frame, and said computed tomography system further comprising a rapid coupling which, in a defined rotational position of said gantry relative to said gantry frame, places said lines from said heat exchanger in fluid communication with said lines from said source and said sink.

5. A computed tomography system as claimed in claim 4 wherein said rapid coupling comprises a magnetic coupling operated by at least one electromagnet.

6. A computed tomography system as claimed in claim 1 wherein said heat exchanger has fluid lines mounted on said gantry, and said computed tomography system further comprising a water outlet for emptying said secondary side of said heat exchanger and said fluid lines.

7. A computed tomography system as claimed in claim 6 further comprising a compressed air source, selectively placeable in fluid communication with said secondary side of said heat exchanger and said lines for forcing said further liquid coolant through said outlet.

8. A computed tomography system as claimed in claim 1 wherein said source of further coolant comprises said sink.

* * * * *